United States Patent [19]

Chaussee

[11] Patent Number: 5,334,325
[45] Date of Patent: Aug. 2, 1994

[54] DELAYED-GELLING, POST-FOAMING COMPOSITION BASED UPON ALKOXYLATED ALKYL PHOSPHATE ESTER SURFACTANTS

[75] Inventor: James G. Chaussee, Racine County, Wis.

[73] Assignee: S. C. Johnson & Son, Inc., Racine, Wis.

[21] Appl. No.: 643,850

[22] Filed: Jan. 23, 1991

[51] Int. Cl.$^5$ .................... C11D 1/78; C11D 3/18; C11D 3/36; C11D 17/00
[52] U.S. Cl. .................... 252/174.16; 252/174.21; 252/90; 252/DIG. 17; 252/DIG. 5; 252/DIG. 13; 252/DIG. 14; 424/43; 424/73
[58] Field of Search ............ 252/DIG. 17, 90, 174.16, 252/174.21, DIG. 5, DIG. 13, DIG. 14; 424/43, 73

[56] References Cited

U.S. PATENT DOCUMENTS

| | | | |
|---|---|---|---|
| 2,995,521 | 8/1961 | Estiguard-Bluard | 252/90 |
| 3,341,465 | 9/1967 | Kaufman et al. | 252/316 |
| 3,541,581 | 11/1967 | Monson | 252/90 |
| 4,772,427 | 9/1988 | Dawson et al. | 252/559 |
| 4,871,530 | 10/1989 | Grollier et al. | 424/47 |
| 4,904,405 | 2/1990 | Kajihara et al. | 252/90 |
| 4,940,577 | 7/1990 | Greenberg et al. | 424/59 |
| 4,968,450 | 11/1990 | Kamegai et al. | 252/545 |

FOREIGN PATENT DOCUMENTS

| | | | |
|---|---|---|---|
| 1021264 | 11/1977 | Canada | 167/304 |
| 1028957 | 4/1978 | Canada | 167/304 |
| 1029306 | 4/1978 | Canada | 167/304 |
| 1444334 | 7/1976 | United Kingdom | C09K 3/30 |
| 2166150 | 4/1986 | United Kingdom | C11D 10/04 |

OTHER PUBLICATIONS

GAF Chemicals Brochure No. 7.5M-189, 1989, 4 pages describing Anionic GAFAC® surfactants.
Surfactants in Cosmetics, M. Rieger, ed., Marcel Dekker, Inc., New York, N.Y., 1985, pp. 366-367.
"Clear Gel Systems, Chapter 6", from Croda, Inc., Brochure titled Croda, pp. 43-44.
"Clear Gel Cosmetics", The Chemistry and Manufacture of Cosmetics, M. G. De Navarre, Van Nostrand, Princeton, N.J., 1962, pp. 1355-1361.

*Primary Examiner*—Paul Lieberman
*Assistant Examiner*—Erin Higgins

[57] ABSTRACT

A delayed-gelling, post-foaming gel composition which is dispensed from an aerosol or piston container in the form of a liquid and remains as a liquid for a predetermined period of time before it sets up into a gel.

14 Claims, No Drawings

DELAYED-GELLING, POST-FOAMING COMPOSITION BASED UPON ALKOXYLATED ALKYL PHOSPHATE ESTER SURFACTANTS

BACKGROUND OF THE INVENTION

1. Field of the Invention

This invention relates to a delayed-gelling, post-foaming composition, suitable for use as a skin or hair cleaner, such as shaving gel or a shampoo, or as a fabric cleaner which can be dispensed from an aerosol or a piston container in the form of a liquid before gelling.

2. Description of the Related Art

Post-foaming gel compositions suitable for use as a skin or hair cleanser are known in the field of cosmetics. These compositions are dispensed from an aerosol or a piston container in the form of a stable gel substantially free from foaming. When the gel is spread over the skin or hair and rubbed, the gel post-foams into a lathered product. Examples of such post-foaming gel compositions are described in U.S. Pat. Nos. 3,541,581 and 4,871,530, British Specification No. 1,444,334, and U.K. Patent Application No. 2,166,150.

These known post-foaming gel compositions have a disadvantage in that when the compositions are dispensed in the form of a stable gel, the gel may not be easily spread over the skin or hair in an even and fluid manner.

It has now been discovered that a composition comprising an anionic alkoxylated alkyl phosphate ester surfactant, a hydrocarbon post-foaming agent, a neutralizing agent, and water can be dispensed from an aerosol or a piston container in the form of a liquid and remains as a liquid for a predetermined period of time to allow for easy application to the skin or hair before the composition gels. Furthermore, the composition is mild to the skin and has cleaning capability. Therefore, it is useful as a skin or hair cleanser.

U.S. Pat. No. 4,904,405 describes a foam-type aerosol composition said to be useful as a skin cleanser containing a phosphate ester surfactant obtained by mixing two alkylphosphate salts and a propellant. This composition, however, does not form a post-foaming gel, and is dispensed from an aerosol container directly in the form of a foam.

SUMMARY OF THE INVENTION

The present invention, therefore, provides a delayed-gelling, post-foaming gel composition which can be dispensed from an aerosol or piston container in the form of a liquid. The composition remains as a liquid for a predetermined period of time to allow for easy application of the liquid to the skin or hair in a fluid and even manner. The liquid then rapidly sets up into a gel until it is rubbed, at which time it post-foams into a lathered product. The present invention also provides a delayed-gelling, post-foaming composition which is mild to the skin and hair and has cleansing ability. Accordingly, it is suitable for use as skin or hair cleanser, such as a shaving gel or shampoo. In addition, the inventive composition can be formulated into a fabric cleaner or used for other cleaning applications.

More specifically, the present invention provides a delayed-gelling, post-foaming gel composition which comprises:

(a) from about 15 to 30 weight percent of an anionic alkoxylated alkyl phosphate ester surfactant;

(b) a sufficient amount of a neutralizing agent to provide a pH for the composition from about 4.5 to 8;

(c) from about 0.5 to 15 weight percent of a hydrocarbon post-foaming agent; and (d) the balance comprising water.

The delayed-gelling, post-foaming composition according to the present invention may also optionally contain various cosmetic additives such as other surfactants, polymers for gel thickening and lubrication, cosmetic esters for emolliency, humectants for moisturization, fragrances, dyes, preservatives, or other active ingredients such as salicylic acid.

DESCRIPTION OF THE PREFERRED EMBODIMENTS

The preferred anionic alkoxylated alkyl phosphate ester surfactant according to the present invention has the general formula:

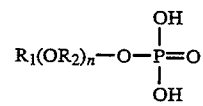

wherein $R_1$ is an alkyl group having about 8 to 18 carbon atoms, preferably about 10 to 16 carbon atoms, and most preferably about 10 to 14 carbon atoms, $(OR_2)$ is an ethoxy or propoxy group; and, the degree of alkoxylation or the number of moles of alkoxy group, n is from about 1 to 10, preferably about 1 to 6.

In general, the lower the number of carbon atoms in the alkyl group $R_1$ of the anionic alkoxylated alkyl phosphate ester, the more irritating to the skin and the less soluble in water the phosphate ester. In contrast, the higher the number of carbon atoms in the alkyl group, the milder to the skin and the thicker and more waxy the resultant product. Accordingly, for best results, $R_1$ should have from about 8 to 18 carbon atoms.

The presence of ethoxy or propoxy groups imparts mildness to the anionic alkyl phosphate ester surfactant. In general, the longer the $(OR_2)$ chain, the greater the water solubility. The presence of the ethoxy or propoxy groups, however, also somewhat reduces the cleaning ability of the surfactant. In general, less than 1 mole of ethoxy or propoxy group in the surfactant provides a product which is unduly irritating to the skin and eyes. When over about 10 moles of ethoxy or propoxy group are present, however, although the surfactant is milder, the cleaning ability is generally unsatisfactory. Accordingly, from about 1 to 6 moles of the ethoxy or propoxy group in the anionic alkoxylated alkyl phosphate ester provide the best results.

The anionic alkoxylated alkyl phosphate ester surfactant is present in the present composition in an amount from about 15 to 30 weight percent, preferably about 22 to 26 weight percent, based on the total weight of the composition. Example of typical anionic alkoxylated alkyl phosphate esters of the invention include $C_8H_{17}(OCH_2CH_2)OPO(OH)_2$, $C_9H_{19}(OCH_2CH_2)_5OPO(OH)_2$, $C_{12}H_{25}(OCH_2CH_2)_3OPO(OH)_2$, $C_{14}H_{29}(OCH(CH_3)CH_2)_2OPO(OH)_2$, $C_{16}H_{33}(OCH_2CH_2)_4OPO(OH)_2$ and $C_{18}H_{37}(OCH(CH_3)CH_2)_6OPO(OH)_2$, A preferred anionic alkoxylated alkyl phosphate ester surfactant according to the present invention is trideceth-6-phosphate which has the following chemical formula:

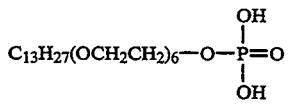

The neutralizing agent according to the present invention is present in an amount sufficient to provide a pH for the composition from about 4.5 to 8, preferably 5 to 6.5. Useful neutralizing agents include sodium hydroxide, ammonium hydroxide, and organic amines. Examples of typical organic amines useful as neutralizing agents include triethanolamine, triethylamine, diethanolamine, diethylamine, monoethanolamine, ethylamine, diisopropanolamine, aminomethyl propanol and aminomethyl propanediol. Ethoxylated amines having the general formula:

wherein R is a hydrocarbon radical having from 10 to 18 carbon atoms and the sum of $x+y$ has an average value of from about 5 to 25 are also useful as neutralizing agents. Examples of such ethoxylated amines include polyoxyethylene (25) cocamine ("PEG-25 cocamine"), i.e., where R are hydrocarbon groups derived from coconut fatty acid and the sum of $x+y$ is about 25; polyoxyethylene ( 5 ) cocamine ( "PEG-5 cocamine"); polyoxyethylene (10) cocamine ("PEG-10 cocamine"); polyoxyethylene ( 15 ) cocamine ( "PEG-15 cocamine"); polyoxyethylene ( 5 ) octadecylamine ( "PEG-5 stearamine"); polyoxyethylene (10) octadecylamine ( "PEG-10 stearamine"); polyoxyethylene (20) octadecylamine; polyoxyethylene ( 25 ) octadecylamine; polyoxyethylene (5) tallowamine ( "PEG-5 tallowamine"); polyoxyethylene ( 15 ) tallowamine ( "PEG-15 tallowamine"); polyoxyethylene ( 5 ) oleylamine ( "PEG-5 oleamine"); polyoxyethylene ( 15 ) oleylamine ( "PEG-15 oleamine"); polyoxyethylene ( 5 ) soyamine ( "PEG-5 soyamine"); polyoxyethylene (10) soyamine ( "PEG-10 soyamine"); polyoxyethylene ( 15 ) soyamine ( "PEG-15 soyamine"); and polyoxyethylene (25) soyamine ("PEG-25 soyamine").

A number of these long chain amines are available commercially under the trade name of ETHOMEEN from Akzo Chemie America, Armak Chemicals of Chicago, Ill. Some amines such as PEG-25 cocamine impart a slight amine odor to the composition which may be masked with a fragrance.

The hydrocarbon post-foaming agent according to the present invention is selected from a mixture of at least one lower hydrocarbon having up to 4 carbon atoms and at least one higher hydrocarbon having between 5 and 8 carbon atoms. Examples of the $C_4$ or lower hydrocarbons include propane, butane and isobutane. Examples of the $C_5$ to $C_8$ higher hydrocarbon include pentane, isopentane, and heptane. While $C_5$ to $C_8$ higher hydrocarbons may sometimes be employed as the post-foaming agent without a $C_4$ or lower hydrocarbon, the resulting product is often less desirable because better foaming and gelling characteristics are obtained if a combination of at least one $C_4$ or lower hydrocarbon and at least one $C_5$ to $C_8$ higher hydrocarbon is used. The $C_4$ or lower hydrocarbons enhance the properties of the foam, while the $C_5$ to $C_8$ higher hydrocarbons enhance the gel integrity.

The amount of post-foaming agent present is generally from about 0.5 to 15 weight percent based on the total weight of the composition. In general, when a higher level of the anionic alkoxylated alkyl phosphate ester surfactant is present, lesser amounts of the hydrocarbon post-foaming agent are needed to form a gel and, conversely, when a lower level of the anionic surfactant is present, greater amounts of post-foaming agent may be needed to form a gel.

When the hydrocarbon post-foaming agent is present in the instant composition at a level of about 15 weight percent, the weight ratio of the $C_5$ to $C_8$ higher hydrocarbons to the $C_4$ or lower hydrocarbons should be less than about 6.5:1. Otherwise, the gel formed is not stable. Conversely, if smaller amounts on the order of about 0.5 weight percent of the post-foaming agent are present in the composition, the weight ratio of the $C_5$ to $C_8$ higher hydrocarbons to the $C_4$ or lower hydrocarbons should be about 1:1. Accordingly, the weight ratio of the $C_5$ to $C_8$ higher hydrocarbons to the $C_4$ or lower hydrocarbons increases as the amount of the post-foaming agent present in the composition increases from about 0.5 to 15 weight percent.

Compressed gases such as liquified petroleum gas, dimethyl ether, nitrogen gas, and nitrogen dioxide gas as well as halogenated hydrocarbons have been found to be undesirable as the post-foaming agent for the present invention because they do not mix well in the inventive composition nor do they promote formation of a stable gel.

The composition according to the present invention may contain other cosmetic additives. For example, the composition may contain from about 0.5 to 2.5 weight percent of at least one hydrocarbon emollient, such as petrolatum and mineral oils of the type known in the art for use in cosmetic compositions. Petrolatum is a preferred emollient. The term "petrolatum" includes mixtures of hydrocarbon materials which resemble petrolatum in appearance and consistency, such as a mixture formed by melting substances such as paraffin wax or microcrystalline wax and the like with mineral oil. More preferably, 0.75 to 2 percent by weight of a hydrocarbon emollient is employed.

From about 0.5 to 2 weight percent of at least one fatty acid ester emollient derived from fatty acids or fatty alcohols having from about 12 to 22 carbon atoms may be employed. Examples of such esters are the methyl, isopropyl and butyl esters of fatty acids such as isopropyl palmitate, isopropyl myristate, isopropyl isostearate, isostearyl isostearate, diisopropyl sebacate, and propylene glycol dipelargonate, as well as 2-ethylhexyl isononoate, 2-ethylhexyl stearate, $C_{12}$–$C_{16}$ fatty alcohol lactates such as cetyl lactate and lauryl lactate, isopropyl lanolate, 2-ethylhexyl salicylate, oleyl myristate, oleyl stearate, oleyl oleate, hexyl laurate, isohexyl laurate and mixtures of the same.

The composition of the invention may further contain from about 0.05 to 1 weight percent, preferably from 0.1 to 0.5 weight percent, of at least one "compatible" surfactant. The term "compatible" as used herein includes a surfactant capable of stabilizing the composition so that the gel does not separate into distinct layers upon storage at room temperature and which does not react with the other ingredients present to result in such a separation. Thus, nonionic surfactants, which typically do not react with other components, may be employed although it may be possible to use anionic or amphoteric surfactants, including zwitterionic surfactants, if they are compatible with the gel composition. An example of such an amphoteric surfactant is oleyl betaine.

An example of useful nonionic surfactants are the polyethoxylated fatty alcohols of the formula R'O(CH$_2$CH$_2$O)$_x$H wherein R' is a hydrocarbon radical of from about 10 to 22 carbon atoms and x has a value of from about 2 to 100 and more preferably, from about 2 to 25. The (R'O) group in the formula can be derived from fatty alcohols having from about 10 to 22 carbon atoms such as lauryl, myristyl, cetyl, hexadecyl, stearyl, isostearyl, hydroxystearyl, oleyl, ricinoleyl, behenyl, and erucyl alcohols, and 2-octadecanol. An example of such surfactant is ceteth-20 (cetyl ether of polyethylene oxide having an average of about 20 ethylene oxide units). This and other such nonionic surfactants are commercially available under the tradename "BRIJ" from ICI Americas, Inc. of Wilmington, Del.

Other examples of nonionic surfactants are those typically used in cosmetics such as alkyl phenols with 6 to 12 carbons in the alkyl chain condensed with 2 to 25 moles of ethylene oxide; mono- and di-fatty acid esters of ethylene glycol wherein the fatty acid moiety contains from about 12 to 22 carbon atoms; fatty acid monoglycerides wherein the fatty acid moiety contains from about 12 to 22 carbon atoms; fatty acid esters of sorbitol, sorbitan, polyoxyethylene sorbitol, and polyoxyethylene sorbitan where the fatty acid moiety contains from about 12 to 22 carbon atoms. Such surfactants are well known and many are commercially available.

The composition may also contain from about 0.5 to 3 weight percent of at least one fatty alcohol having from 10 to 22 carbon atoms. The same alcohols specified for use in the above polyethoxylated alcohols can be employed by themselves as this component of the composition. A 2:1 to 5:1 by weight blend of cetyl alcohol to myristyl alcohol has been found to be useful with the 5:1 blend being presently preferred. Stearyl alcohol has also been found to be useful. More preferably, the total fatty alcohol content in the compositions is from about 1 to 2.5 weight percent.

The present composition may further comprise from about 0.5 to 9 weight percent of alkanolamides of fatty acids. The fatty acid may be any long-chain aliphatic acid of 12-22 carbon atoms. The alkanol group is preferably a lower alkanol, e.g., ethanol or methanol. The alkanolamides of fatty acids are employed because they contribute to the preparation of a clear, sparkling, and aesthetically pleasing product. A preferred alkanolamide for the present invention is lauroyl monoethanolamide.

Humectants may be present in amounts from about 1 to 10 weight percent and typically include water-soluble polyhydric alcohols having from 2 to 3 hydroxyl groups such as 1,2-propylene glycol, dipropylene glycol, polyethylene glycol of molecular weight up to about 6,000, 1,3-butylene glycol, 1,2,6-hexanetriol, glycerine and mixtures thereof. Glycerine is presently preferred. It is preferred to employ the humectant in amounts from about 2 to 4 weight percent of the total composition.

Water comprises the balance of the composition. Deionized water is preferred. There should be a sufficient amount of water to provide a thickened gel composition after dispensing from a container. Generally, at least about 20 weight percent of the composition should be water, more preferably at least about 25% and most preferably, at least about 28%.

To improve lubricity, a silicone fluid such as a dimethylpolysiloxane or other conventional organopolysiloxanes can be used in amounts of from about 0.05 to 1 weight percent. In general, the viscosity of the silicone fluid at a temperature of 25° C. is from about 5 centistokes to about 12,500 centistokes ($5 \times 10^{-6}$ to $1.25 \times 10^{-2}$ square meters per second—"m$^2$/sec") . Typical organopolysiloxanes which can be used are dimethylpolysiloxane (CTFA name—dimethicone which is a dimethylpolysiloxane end-blocked with trimethylsiloxy units), diethylpolysiloxane, dimethyldiphenylpolysiloxane, and the like. Volatile linear and cyclic polydimethylsiloxanes such as hexamethyldisiloxane, polydimethylcyclosiloxane (CTFA name—cyclomethicone), and trimethylsilyl end-blocked polydimethylsiloxane having a viscosity in the range of from about 0.65 centistokes to about 5 centistokes ($6.5 \times 10^{-7}$ to $5 \times 10^{-6}$ m$^2$/sec) can also be included as part of the silicone fluid content.

Other conventional additives to cosmetic compositions such as fragrances, dyes, preservatives, polymers, etc., can also be included provided that they are compatible with the gel composition.

The composition according to the present invention may also contain active ingredients such as salicylic acid, which imparts anti-acne treatment characteristics to the resultant gel composition. Preferably, the amount of salicylic acid present is from about 0.5 to 2.0 weight percent based on the total weight of the composition.

The delayed-gelling, post-foaming gel composition according to the present invention, when dispensed from an aerosol or a piston container in the form of a liquid, usually remains as a liquid from about 5 to 80 seconds, preferably 5 to 30 seconds, before it rapidly sets up into a gel.

The preferred aerosol container for the present invention is a two-compartment type aerosol container. An example of such container is a Sepro TM container which is shown in FIG. 4 of U.S. Pat. No. 3,541,581. In such a container, the delayed-gelling, post-foaming gel composition is contained within a collapsible or expandable bag within the container separate from a bottom compartment which is pressurized with a necessary amount of a propellant, which serves to expel the gel composition from the container. Another example of a two-compartment type aerosol container is a piston container of the type described in U.S. Pat. No. 4,913,323.

Suitable propellents useful in pressurizing the container described above include the condensable gaseous propellents ordinarily utilized in the manufacture of aerosol compositions. For example, suitable propellents include hydrocarbon propellents, such as propane, butane, isobutane, and isopentane. Environmentally hazardous halogenated hydrocarbon propellents which can be represented by the structural formula C$_n$H$_x$Cl$_y$F$_z$, wherein n is a whole number form 1 to 2 and x, y and z is equal to 2n+2 can be employed, but, of course, are not preferred in view of their known environmental effects.

Mixtures of various propellents and diluents are often employed to obtain the desired vapor pressure with the container. In addition to the various condensable gaseous propellents discussed above, propellents suitable for the present invention can comprise noncondensable gases such as nitrous oxide or nitrogen and mixtures thereof.

The following Examples are provided to show various aspects of the invention without departing from the scope and spirit of the invention. Unless otherwise indicated, all parts and percentages used in the Examples are by weight.

EXAMPLES 1-5

The following formulations were prepared to illustrate how the inventive compositions exhibit delayed gelling after dispersing from a container and the effect of pH levels on gel firmness. Initially, an intermediate was prepared which contained water, an anionic alkoxylated alkyl phosphate ester surfactant, a neutralizing agent and cosmetic additives. Thereafter, the intermediate was pressurized with the post-foaming agent.

In the following examples the anionic alkoxylated alkyl phosphate ester surfactant employed was Trideceth-6-phosphate; the neutralizing agent was triethanolamine; and the post-foaming agent was a blend of isobutane and pentane.

The composition of the intermediate (1) to (5) prepared for Example 1-5 is as follows:

| Ingredients | INTERMEDIATE | | | | |
| --- | --- | --- | --- | --- | --- |
| | Example 1 | Example 2 | Example 3 | Example 4 | Example 5 |
| 1/GAFAC RS-610 | 23.89 | 23.89 | 23.89 | 23.89 | 23.89 |
| 2/Clindrol 100ML95 | 0.75 | 0.75 | 0.75 | 0.75 | 0.75 |
| Propylene glycol | 10.00 | 10.00 | 10.00 | 10.00 | 10.00 |
| Cyclomethicone | 2.00 | 2.00 | 2.00 | 2.00 | 2.00 |
| Triethanolamine | 5.01 | 5.57 | 6.41 | 7.80 | 10.58 |
| 3/Velvetex OLB-30 | 1.67 | 1.67 | 1.67 | 1.67 | 1.67 |
| 4/Roure W4151 | 0.10 | 0.10 | 0.10 | 0.10 | 0.10 |
| Deionized Water | 56.58 | 56.02 | 55.18 | 53.79 | 51.01 |
| Total | 100.00 | 100.00 | 100.00 | 100.00 | 100.00 |
| pH | 4.7 | 5.9 | 6.4 | 7.0 | 7.8 |

1/Trideceth-6-phosphate available from GAF Corporation.
2/A high purity lauroyl monoethanolamide available from Clintwood Chemical Company.
3/30% active oleyl betaine - an amphoteric surfactant.
4/A type of fragrance.

Each of the Example 1-5 intermediates was then mixed with the following post-foaming agent at the levels indicated. Accordingly, for each intermediate (1)-(5) three delayed gelling, post-foaming compositions, A, B and C were prepared with gradually increasing amounts of post-foaming agent. Therefore, 15 compositions were prepared, three for each of Examples 1-5 and identified as 1A, 1B, 1C for Example 1 to 5A, 5B and 5C for Example 5, as follows:

| Composition | Amount Intermediate | Amount Post-Foaming Agent | |
| --- | --- | --- | --- |
| | | Pentane | Isobutane |
| Ex. (1-5) A | 98.2 | 1.1 | 0.7 |
| Ex. (1-5) B | 98.05 | 1.25 | 0.7 |
| Ex. (1-5) C | 97.9 | 1.4 | 0.7 |

Such delayed-gelling, post-foaming compositions were prepared by charging all the ingredients of the intermediates, except the fragrance and cyclomethicone, to a container with continued mixing until the resulting blend was thoroughly dispersed and uniform. The blend was then heated to approximately 150° F. to melt the Clindrol 100ML 95 followed by cooling to 100° F. with agitation. Cyclomethicone and the fragrance were then added, and cooling with agitation was continued to room temperature. The intermediate was then allowed to deaerate, and then weighed and charged into a 2-compartment aerosol Sepro ™ container followed by a weighed charge of pentane.

The valve of the container was then vacuum crimped and isobutane was then added through the valve stem. The container was then shaken vigorously for approximately 20 seconds to disperse the hydrocarbon and then pressurized through the grommet at the bottom of the container with 15 to 25 cc. of isobutane.

The resultant gel firmness and gel set times for the compositions (1-5) A, (1-5) B and (1-5) C were then determined, and the results are shown below in Table 1.

TABLE 1

| Examples | PH | Gel Firmness | Gel Set Times (sec) | | |
| --- | --- | --- | --- | --- | --- |
| | | | Post-Foaming agent levels | | |
| | | | A | B | C |
| 1 | 4.7 | Soft | 75-80 | 40-45 | 20-30 |
| 2 | 5.9 | Medium | 15-20 | 10-15 | 5 |
| 3 | 6.4 | Hard | 10 | 5-10 | 5 |
| 4 | 7.0 | Hard | <5 | <5 | <5 |
| 5 | 7.8 | Medium | 40 | 30 | 15 |

From the test results it is apparent that the pH and amount of post-foaming agent impact on the gel firmness and gel set times. At higher pH's the gels tend to be harder and the gel set times slower. At higher post-foaming agent levels the gel also tends to set faster. All gel firmness values have been determined subjectively and categorized.

EXAMPLE 6

An intermediate of the invention was prepared in accordance with the procedure of Example 1 with the exception that triethylamine was employed as the neutralizing agent as follows:

| Ingredients | Intermediate |
| --- | --- |
| GAFAC RS-610 | 23.89 |
| Clindrol 100Ml 95 | 0.75 |
| Propylene glycol | 10.00 |
| Cyclomethicone | 2.0 |
| Triethylamine | 3.86 |
| Velvetex OLB-30 | 1.67 |
| Roure W4151 | 0.1 |
| Deionized Water | 57.73 |
| Total | 100.00 |
| pH | 6.0 |

The intermediate was then mixed with the following post-foaming agent to form a gel composition of the invention at the indicated post-foaming agent levels.

| Composition | Amount Intermediate | Amount Post-Foaming Agent | |
| --- | --- | --- | --- |
| | | Pentane | Isobutane |
| 6D | 98.2 | 1.1 | 0.7 |

-continued

| Composition | Amount Intermediate | Amount Post-Foaming Agent | |
|---|---|---|---|
| | | Pentane | Isobutane |
| 6E | 98.03 | 1.27 | 0.7 |
| 6F | 97.89 | 1.41 | 0.7 |

The resultant gel firmness and gel set times at the three post-foaming agent levels were then determined, and the results are shown below in Table 2.

TABLE 2

| Gel Firmness | Gel Set Times (Sec.) Post-Foaming agent levels | | |
|---|---|---|---|
| | 6D | 6E | 6F |
| Medium | 15–20 | 10–15 | 5 |

EXAMPLE 7

In order to illustrate the inventive compositions which include additional cosmetic additives the following delayed-gelling, post foaming formulations were prepared in accordance with the procedure provided hereafter.

| Ingredients | Intermediate |
|---|---|
| GAFAC RS-610 | 22.5 |
| 5/Cyclomide L-203 | 1.8 |
| Propylene glycol | 10.35 |
| Cyclomethicone | 3.9 |
| Triethanolamine 85% | 5.25 |
| Velvetex OLB-30 | 1.47 |
| 6/CO-1214 Fatty Alcohol | 0.5 |
| 7/SDA 40A Alcohol | 2.0 |
| 8/Surfadone LP100 | 2.0 |
| 9/Fragrance A 40466A | 0.5 |
| Deionized Water | 49.73 |
| Total | 100.00 |
| pH | 6.0 |

5/Lauroyl monoethanolamide available from Cyclo Corporation.
6/Fatty Alcohol available from Procter & Gamble.
7/Denatured Alcohol.
8/N-octyl pyrrolidone - a nonionic surfactant available from GAF Corporation.
9/A type of fragrance.

The above intermediate was then mixed with the following post-foaming agent at the indicated levels to provide the indicated delayed-gelling, post-foaming compositions.

| Ingredient | Amount |
|---|---|
| Intermediate | 94.8–96.3 |
| Pentane | 3.0–4.5 |
| Isobutane | 0.7 |

The resultant gel firmness and gel set times were then determined, and the results are shown below.

| Gel Firmness | Gel Set Time |
|---|---|
| Medium | <30 Sec. |

Similar results are obtained when Deceth-4 Phosphate and Sodium Laureth-4 Phosphate are substituted for the Trideceth-6 Phosphate (GAFAC RS-610). Deceth-4 Phosphate is also known as GAFAC RA-600 (or Cyclophos PL6A) and has the formula $C_{10}H_{21}(OCH_2CH_2)_4OPO(OH)_2$. Sodium Laureth-4 Phosphate is also known as GAFAC MC-470. Both such anionic ethoxylated alkyl phosphate surfactants are available from GAF Corporation, now a part of Rhone-Poulenc.

The above compositions were prepared by charging all the ingredients of the intermediate except the fragrance, SDA 40A Alcohol, and cyclomethicone into a container with continued mixing until the resulting blend was thoroughly dispersed and uniform. The blend was then heated to approximately 150° F. to melt the Cyclomide L-203 followed by cooling to 100° F. with agitation. Cyclomethicone, SDA 40A Alcohol, and fragrance were then added, and cooling with agitation was continued to room temperature.

The intermediate was then allowed to deaerate, and then weighed and charged into a 2-compartment aerosol Sepro ™ container followed by a weighed charge of pentane. The valve of the container was then vacuum crimped and isobutane was then added through the valve stem. The container was then shaken vigorously for approximately 20 seconds to disperse the hydrocarbon and then pressurized through the grommet at the bottom of the container with 15 to 25 cc. of isobutane.

COMPARATIVE EXAMPLE 1

In order to demonstrate the effects of changing the pH level on delayed gelling, post-foaming gel compositions an intermediate was prepared according to Example 1, a post-foaming agent was thereafter added and the composition was dispensed as follows:

| Ingredients | Intermediate |
|---|---|
| GAFAC RS-610 | 23.89 |
| Clindrol 100 ML 95 | 0.75 |
| Propylene glycol | 10.00 |
| Cyclomethicone | 2.00 |
| Triethanolamine | 4.73 |
| Velvetex OLB-30 | 1.67 |
| Roure W4151 | 0.1 |
| Deionized water | 56.86 |
| Total | 100.00 |
| pH | 3.9 |

The above intermediate was then mixed at the same three post-foaming agent levels described in Examples 1–5. At the indicated pH value of 3.9, no gels were formed, when the formulation was dispensed from a Sepro ™ type container.

COMPARATIVE EXAMPLE 2

The effect of substituting other nonionic surfactants in delayed gelling, post-foaming compositions for the alkoxylated alkyl phosphate ester surfactants was investigated. Compositions employing nonyl phenol phosphates in place of the instant alkoxylated alkyl phosphate ester were tested. While capable of forming gels, the compositions containing nonyl phenol phosphates did not provide the requisite delay in gel formation provided by the instant alkoxylated alkyl phosphates. Typical nonyl phenol phosphates which do not exhibit a delay in gel formation upon dispensing include the GAFAC RM anionics having the formula $(C_9H_{19})_2C_6H_3(OCH_2CH_2)_nOPO(OH)_2$; GAFAC RE-610 of the formula $[C_9H_{19}C_6H_4(OCH_2CH_2)_n]OPO(OH)_2$, when n has a value of 9 and Nonoxynol-6 Phosphate of the formula $CH_3(CH_2)_7CHC_6H_4(OCH_2CH_2)_6OPO(OH)_2$.

Typical artionic surfactants which failed to form adequate gels include the AKYPO carboxylates

[C$_{12}$H$_{25}$ (OCH$_2$CH$_2$)$_n$CH$_2$COOH, and the MONATERGE 85-HF which is a blend of Cocamide DEA, DEA-C21--Dicarboxylate and C$_{12}$H$_{25}$C$_6$H$_4$SO$_3$H. Finally, the PPG-5-Ceteth-10 Phosphate of the formula, CH$_3$(CH$_2$)$_{14}$CH$_2$[OCH(CH$_3$)CH$_2$]$_5$(OCH$_2$CH$_2$)$_{10}$ OPO(OH)$_2$ provided either unduly soft gels or separated on dispensing and failed to form any gel.

While the present invention has been described with respect to what is presently considered to be the preferred embodiments, it is to be understood that the invention is not limited to the disclosed embodiments. The present invention is intended to cover various modifications and equivalent formulations included within the spirit and scope of the appended claims.

What is claimed is:

1. A delayed-gelling, post-foaming composition which comprises:
   (a) from about 15 to 30 weight percent of an anionic alkoxylated alkyl phosphate ester surfactant having the general formula

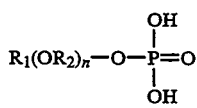

wherein R$_1$ is an alkyl group having about 8 to 18 carbon atoms, (OR$_2$) is an ethoxy or a propoxy group, and n is from about 1 to 10;
   (b) a sufficient amount of a neutralizing agent to provide a pH for the composition of from about 4.5 to 8;
   (c) from about 0.5 to 15 weight percent of a post-foaming agent selected from the group consisting of at least one higher hydrocarbon having between 5 to 8 carbon atoms and a mixture of at least one lower hydrocarbon having up to 4 carbon atoms and at least one higher hydrocarbon having between 5 to 8 carbon atoms; and
   (d) the balance comprising water, wherein the composition is dispensed from a container in the form of a liquid and remains as a liquid for a predetermined period of time before it sets up into a gel.

2. A delayed-gelling, post-foaming composition according to claim 1, wherein R$_1$ is an alkyl group having 10 to 16 carbon atoms.

3. A delayed-gelling, post-foaming composition according to claim 2, wherein R$_1$ is an alkyl group having 10 to 14 carbon atoms.

4. A delayed-gelling, post-foaming composition according to claim 1, wherein (OR$_2$) is an ethoxy group.

5. A delayed-gelling, post-foaming composition according to claim 2, wherein n is from about 1 to 6 moles.

6. A delayed-gelling, post-foaming composition according to claim 1, wherein said neutralizing agent is selected from the group consisting of an organic amine, sodium hydroxide or ammonium hydroxide.

7. A delayed-gelling, post-foaming composition according to claim 1, wherein said neutralizing agent is triethanolamine.

8. A delayed-gelling, post-foaming composition according to claim 1, wherein said neutralizing agent is present in an amount sufficient to provide a pH from about 5 to 6.5.

9. A delayed-gelling, post-foaming composition according to claim 1, wherein said hydrocarbon post-foaming agent is selected from a mixture at least one lower hydrocarbon having up to 4 carbon atoms and at least one higher hydrocarbon having between 5 to 8 carbon atoms.

10. A delayed-gelling, post-foaming composition according to claim 9, wherein said hydrocarbon post-foaming agent is a mixture of isobutane and pentane.

11. A delayed-gelling, post-foaming composition according to claim 1, which further comprises at least one additive selected from the group consisting of from about 0.5 to 2.5 weight percent of at least one hydrocarbon emollient, from about 0.5 to 2 weight percent of at least one cosmetic fatty acid ester emollient, from about 0.5 to 3 weight percent of at least one fatty alcohol having from 10 to 22 carbon atoms, from about 0.5 to 9 weight percent of at least one alkanolamide of a long-chain fatty acid having from 12 to 22 carbon atoms, and from about 1 to 10 weight percent of a humectant, or mixtures thereof.

12. A delayed-gelling, post-foaming composition according to claim 1, wherein the composition further contains from about 0.5 to 2.0 weight percent based upon the total weight of the composition of salicylic acid.

13. A delayed-gelling, post-foaming composition according to claim 1, wherein said composition remains as a liquid for about 5 to 80 seconds.

14. A delayed-gelling, post-foaming composition according to claim 1, wherein said composition remains as a liquid for about 5 to 30 seconds.

* * * * *